(12) United States Patent
Hanna

(10) Patent No.: US 6,252,661 B1
(45) Date of Patent: *Jun. 26, 2001

(54) OPTICAL SUB-PIXEL PARTS INSPECTION SYSTEM

(76) Inventor: James L. Hanna, 2847 Quail Hollow Ct., Ann Arbor, MI (US) 48108

( * ) Notice: Subject to any disclaimer, the term of this patent is extended or adjusted under 35 U.S.C. 154(b) by 0 days.

This patent is subject to a terminal disclaimer.

(21) Appl. No.: 09/366,026

(22) Filed: Aug. 2, 1999

(51) Int. Cl.[7] ................................................. G01B 11/04
(52) U.S. Cl. ............................................ 356/385; 356/394
(58) Field of Search ............................... 356/385, 394, 356/376, 383–387; 250/559.12, 559.13, 559.19

(56) References Cited

U.S. PATENT DOCUMENTS

| 2,812,685 | 11/1957 | Vossberg . |
| 4,067,652 | 1/1978 | Bohlander . |
| 4,260,260 | 4/1981 | Letort et al. . |
| 4,532,723 | 8/1985 | Kellie et al. . |
| 4,880,991 | 11/1989 | Boehnlein et al. . |
| 5,164,995 | 11/1992 | Brooks et al. . |
| 5,383,021 | 1/1995 | Hanna . |
| 5,568,263 | 10/1996 | Hanna . |
| 5,608,530 | 3/1997 | Gates . |
| 5,786,894 | * 7/1998 | Shields et al. ........................ 356/338 |

\* cited by examiner

Primary Examiner—Robert H. Kim
Assistant Examiner—Layla Lauchman
(74) Attorney, Agent, or Firm—Brinks Hofer Gilson & Lione

(57) ABSTRACT

An inspection system for evaluating workpieces for conformance to configuration criteria including a track for causing workpieces to translate through a test section, the test section including a light source for production of a uniform sheet of light, the light source oriented with respect to the track means such that the workpieces occlude the uniform sheet of light upon passing through the test section, the test section further having a video system for receiving the occluded uniform sheet of light, providing output signals related to the intensity of the occluded uniform sheet of light incident on the video system, and a signal processing means for receiving the output signals.

19 Claims, 3 Drawing Sheets

OPTICAL SUB-PIXEL PARTS INSPECTION SYSTEM

BACKGROUND OF THE INVENTION

The present invention relates to a device for inspecting components and particularly to one using an array of light sources and video devices as a means of evaluating a component for conformance to spatial form criteria.

Presently, there is an ever increasing demand to obtain high quality products which has resulted in a significant increase in the use of non-contact inspection systems. In order for a complex machine to operate as designed, it is necessary that all of its sub-components comply with quality criteria. In some manufacturing settings, customers require 100% inspection of component parts. For example, fasteners used in the automobile industry and elsewhere often must be individually inspected to determine if they meet spatial form criteria.

Numerous types of inspection systems are presently utilized. One type of system uses contact probes which touch a component at various points to determine if its dimension or profile meet certain criteria. However, contact devices have inherent limitations in that they are subject to wear and generally require that the component and the contract probe be accurately positioned during the evaluation process. Moreover, such devices are generally slow to operate and are limited in terms of the number of criteria and complexity of profiles which they can evaluate. A variety of non-contact systems are also known using a variety of techniques. For example, ultrasonic inspection systems examine reflected sound waves as a means of characterizing a component. Various systems based on photodetection utilizing single channel photodetectors are also known. In addition, laser gauging systems are used in which specific dimensional measurements can be obtained.

However, although known non-contact inspection systems are generally extremely useful, they have certain limitations. Many of the presently available non-contact gauging systems require complex data processing approaches which impose speed limitations in part evaluations. For example, systems utilizing two-dimensional photosensitive arrays impose extreme data processing requirements, which has the effect of reducing part throughput. Preferably, evaluation of a workpiece can be conducted in a rapid enough fashion that the parts can be directly sorted into qualified or disqualified part streams. The systems which are capable of such high speed inspection lack valuable signal processing capabilities such as edge detection and real time imaging. Edge detection enhances the accuracy of the inspection enabling the parts inspection system to overcome the inherent limitations of discrete photodetectors. Early photodetection systems and ultrasonic systems provided part shape information based on the signal strength of a transducer. This information was only an approximation of the parts shape and not a true image of the part. For example single channel photodetectors could generate a single output related to the amount of occluded light. Over a set period of time this single channel photodetector gives an approximation of the part shape, but not an actual picture of the part. There is a need in the art for a high speed inspection system with powerful signal processing capabilities which include edge detection and real time imaging.

SUMMARY OF THE INVENTION

In accordance with the present invention, an improved non-contact inspection system is provided which enables rapid inspection to be conducted permitting parts to be immediately sorted in terms of being in conformance or out of conformance with spatial form criteria. Moreover, a hard copy of part geometry can be generated from a shadow image or occluded light profile of the part pointing out specific shape discrepancies. For example, for a threaded fastener, the diameter, length, profile and threads can be evaluated. When producing fasteners, the process often begins with wire stock which is fed into a cold heading or screw type forming machine. The part is die-formed or cut in a machine into a shape that may include several diameters and possibly a threaded or knurled length. The formed part may require secondary operations such as thread rolling, heat treating, planing, etc. It is not uncommon for one or more of the processes to fail to produce the desired geometry of part. The occurrence of such defects is often not adequately monitored through random part selection or other quality assurance processes which do not provide a 100% inspection.

In the present invention parts move by gravity or other means along a track through a test section. The part shape is determined through use of a CCD line array/camera, although any type of photodetector may be used. A collimated uniform light source in the form of a sheet is generated in the proximity of the part to be inspected. This uniform sheet of light will allow a highly detailed part examination. The extent and time to which the sheet of light is occluded by the part is related to its shape. As the part moves through the test section containing the CCD line array, the CCD line array will measure the occluded light and generate an output signal to a signal processor. The signal processor will measure the time the part takes to pass over the CCD line array and combine this time information with the occluded light output signal to generate an image of the part. The part measurements of interest are its length and various radial profiles.

A part detection array utilizes a plurality of light sources and CCD line arrays in a radial arrangement around the part to be examined. The part detection array will measure the occluded light from a matched or paired light source which is proximate to the part. In the preferred embodiment of the invention a light source is coupled to a diffractive beam shaper which provides a uniform sheet of light. The uniform sheet of light is used to attain an even intensity pattern over a certain area. The shadows created by the parts because of the use of the uniform sheet of light are indistinct and lack sharp transitions to the lighted areas. In order to interpret these blurred shadow edges special software detailed below has been created to define the location of the actual edge. Each light source used in the array will emit only a certain frequency of light and each CCD line array will include a filter to allow only its matched frequency to be detected. In this manner there will be no cross-talk generated between each light source and its matched CCD line array.

Further objects, features, and advantages of the invention will become apparent from a consideration of the following description and the appended claims when taken in connection with the accompanying drawings.

BRIEF DESCRIPTION OF THE DRAWINGS

The various advantages of the present invention will become apparent to those skilled in the art after reading the following specification and by reference to the drawings, in which.

DETAILED DESCRIPTION OF THE PREFERRED EMBODIMENT

Figure 1:
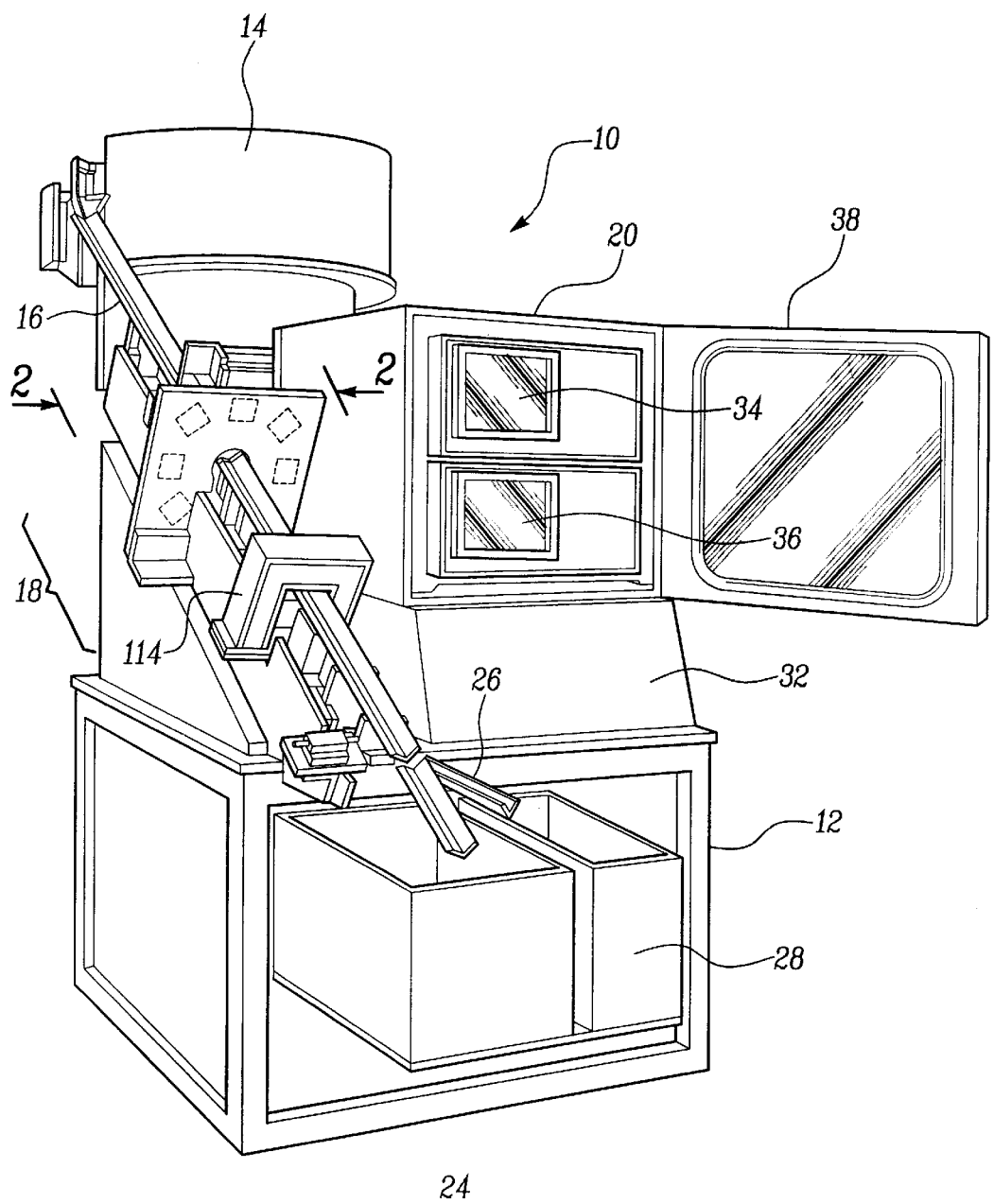
FIG. 1 is a perspective view of the non-contact inspection system according to this invention.

FIG. 1 shows a non-contact inspection system in accordance with the present invention and is generally shown as 10. Inspection system 10 generally comprises frame 12, parts sorter bin 14, slide track 16 having test section 18, and enclosure 20 for housing electronic components of the instrument.

Figure 4:
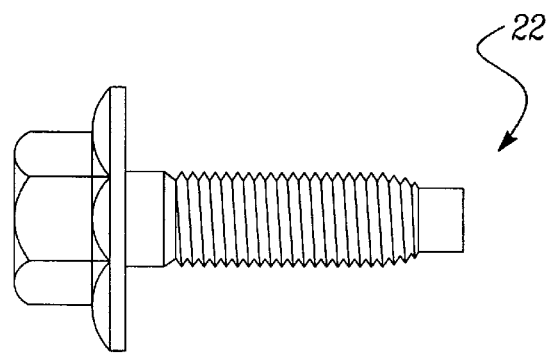
FIG. 4 is an elevational view of a representative workpiece.

While inspection system 10 can be used for numerous types of workpieces, an example of one such component is provided in FIG. 4 in the form of a threaded bolt 22 used for mounting the road wheels of a motor vehicle. A large number of bolts 22 (referred to as "parts" or "work-pieces") are dumped into parts sorter bin 14. Parts sorter bin 14 causes the randomly oriented parts 22 to be directed in a desired orientation i.e. headed or threaded end first, and causes them to periodically slide down track 16 under the force of gravity. As parts 22 pass through test section 18, they are evaluated as will be described in more detail in the following portions of this specification. Part 22 is inspected for conformance with predetermined spatial form criteria. If a particular part meets the criteria, it passes into parts bin 24 provided for qualified or "good" parts. If, however, the part is deemed to be out of conformance, gate 26 is actuated and the part is diverted into parts bin 28 provided for disqualified or "bad" parts. Presumably, good parts will outnumber bad parts and the parts bins are sized accordingly.

Within enclosure 20 is housed computer 32 provided for evaluating the outputs of the system, controlling the system, and providing a means of storing data related to part criteria and inspection history. A pair of displays 34 and 36 is provided, one of which may output in graphical from configuration data for a particular part, whereas the other may be used for outputting statistical or other numerical data related to inspection. In one embodiment of this invention, displays 34 and 36 were electroluminescent types having touch screens for interaction with the user. Enclosure 20 has access doors 38 which can be closed when the system is not in use.

Details of the elements and operations of test section 18 will be described with reference to FIGS. 1 and 2. Within test section 18, evaluations of part 22 profiles are provided. The length of the part 22 (i.e. its dimensions along its direction of travel) and various radial profiles (i.e. its form perpendicular to its direction of travel) are evaluated by a plurality of profile detection arrays.

Figure 2:
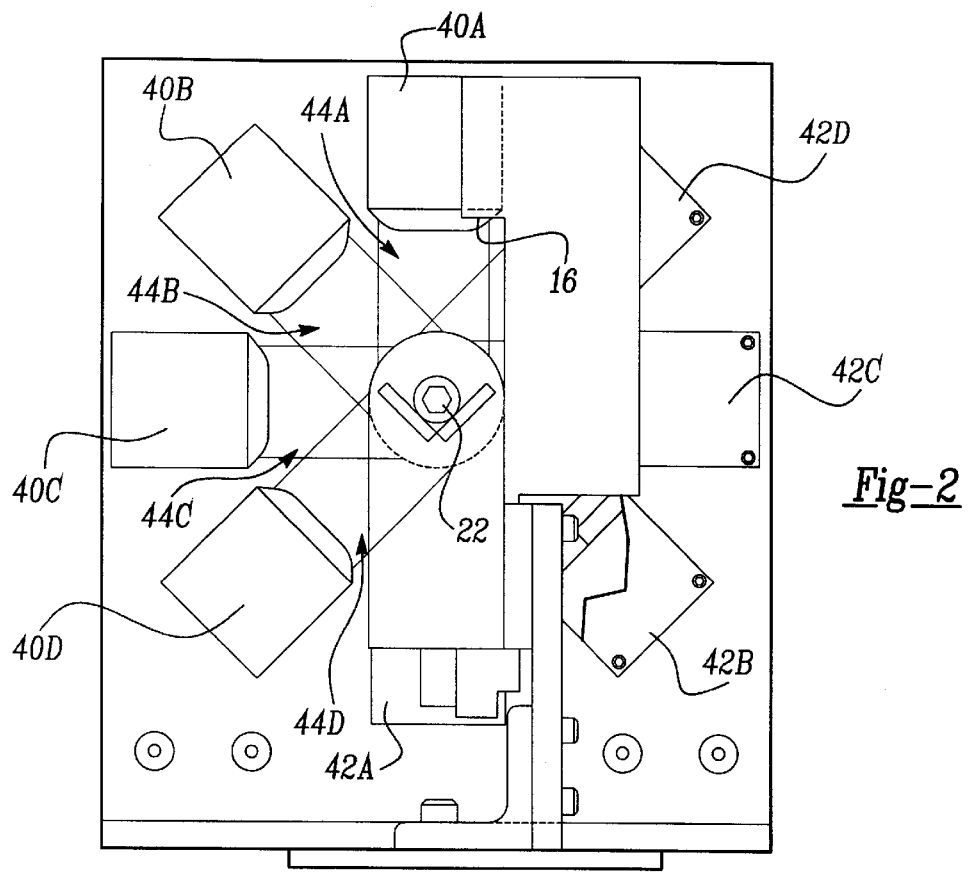
FIG. 2 is a view taken along line 2—2 of FIG. 1 particularly showing the test section.

The profile detection arrays include light sources 40 and CCD line arrays or line scan cameras 42, as shown in FIG. 2, although any type of photodetector may be used. The light sources 40 provides a uniform sheet of light 44 which the part 22 occludes as it travels through test section 18. The extent and time to which this uniform sheet 44 is occluded by the part 22 is related to its shape. As the part 22 moves through the test section the CCD line arrays 42 will measure the occluded light and generate an output signal and direct that output signal to a signal processor.

Figure 5:
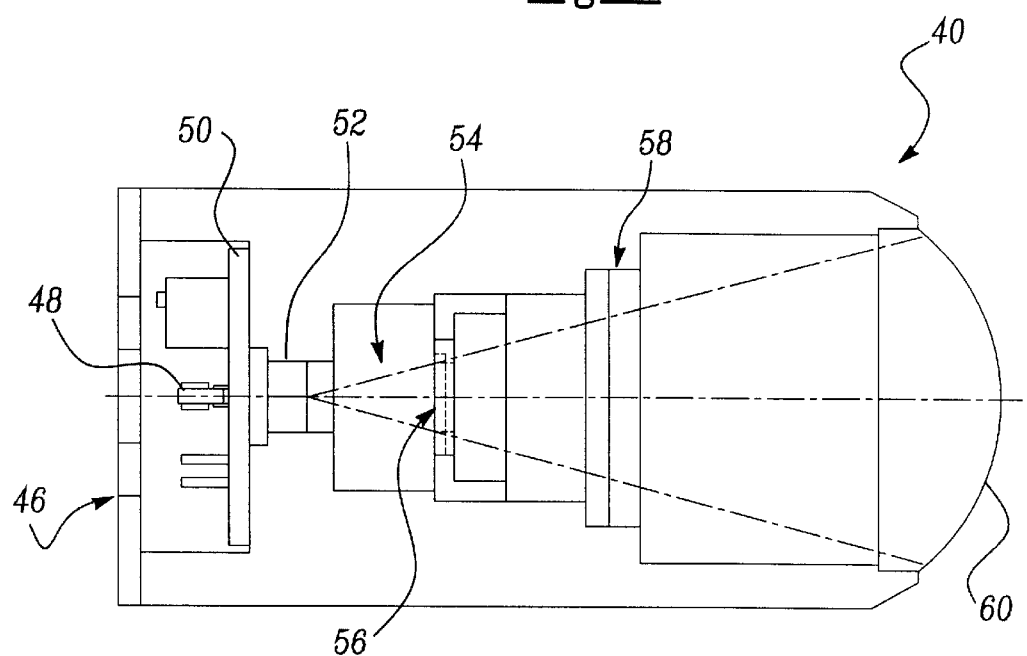
FIG. 5 is a diagrammatic drawing of the light source used in the present invention.

Referring to FIG. 5, the preferred embodiment of the light source 40 is detailed. A framework 46 supports and encloses control and power circuitry including a laser control board 48 and a glass board 50 for the light source 40. A laser diode 52 has a power intensity which is controlled by the laser control board 48 which may be further connected to an external control system by a data communication link so that it may be integrated into a manufacturing line. Although a laser diode 52 is shown, any other type of light or laser light generator such as alternate semiconductor lasers, gas lasers, solid state lasers, and liquid dye lasers may be used with the present invention.

The laser diode 52 generates laser light 54 which is incident upon a diffractive beam shaper 56 that maps an input intensity distribution to an output intensity distribution. The diffractive beam shaper 56 may include gratings, prisms, grisms, lenses, and interferometers to create the desired fringe patterns and intensity distributions. The fringe patterns will vary in width and orientation, depending on the diffractive beam shaper's 56 characteristics. By designing the diffractive beam shaper 56 with an appropriate fringe pattern, one can reflect light into different directions based on the equations describing the different characteristics of the diffractive beam shaper 56.

Figure 6:
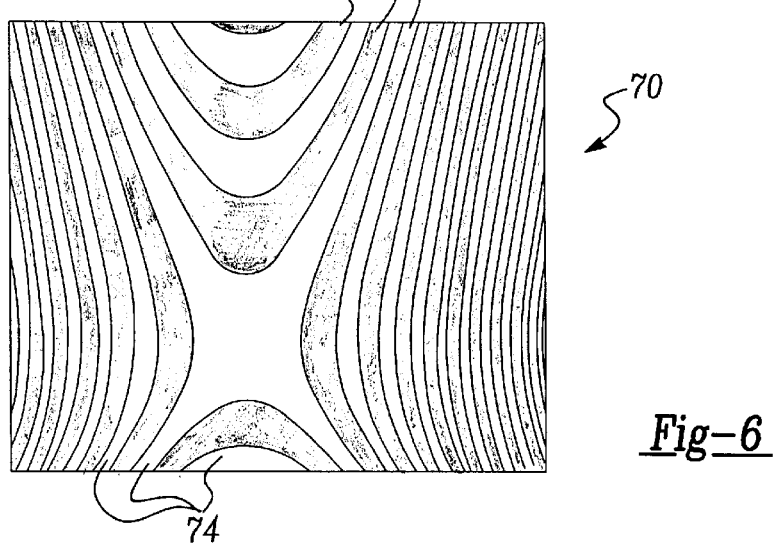
FIG. 6 is a magnified view of one embodiment of a grating used in the present invention having an etched surface.

FIG. 6 illustrates one embodiment of the diffractive beam shaper 56 of the present invention as an etched glass grating 70. The surface of the glass grating 70 has been magnified to show the etched 72 and nonetched 74 regions. The etched regions 72 are represented as darker areas and the nonetched regions 74 are represented as lighter areas. The grating 70 operates as follows: rays of light are deflected at larger angles where the nonetched 74 regions are narrower and close together, and are deflected by smaller angles where the nonetched regions 74 are wider and farther apart. In this way the incident light can be evenly distributed as it exits the grating 70. The etched 72 and nonetched 74 regions have dimensions with magnitudes corresponding to the chosen light wavelengths incident upon the grating 70. For example, the width of one of the nonetched regions 74 may be one wavelength.

One application of the diffractive beam shaper 56 of the present invention, is to take a Gaussian input (i.e. a Gaussian intensity distribution on the aperture of a beam shaper) and map that to a "top hat" distribution (an ideal top hat intensity distribution has only one intensity value inside a certain radius and zero intensity value outside that radius). The function can be thought of as a general ray deflection function. The most intense light at the center of the Gaussian input is deflected radially outward, while the light in the tail of the Gaussian is deflected slightly inward. In this way the intensity of the output beam can be tailored.

After exiting the diffractive beam shaper 56, the laser light 54 is further conditioned by a refractive spherical or cylindrical lens 58. The lens 58 reduces the divergence of the laser light 54 and therefor reduces the need to manufacture more precise diffraction devices in the diffractive beam shaper 56. Additionally, a conventional refractive element might also be used to roughly collimate the output beam. The laser light 54 will finally be conditioned by a convex lens 60 in order to focus the laser light 54. The output of the light source 40 will then comprise a uniform sheet of light 44. By combining diffractive beam shapers and conventional refractive devices, one can produce a family of intensity distributions such as a line that varies as a Gaussian distribution across its width but has a uniform intensity along its length.

As discussed previously in the operation of the inspection system 10, a part 22 will occlude a portion of the light rays and create a shadow against the CCD line arrays 42. The shadows created by the parts are indistinct and lack sharp transitions to the lighted areas. In order to interpret these blurred shadow edges special software has been created to define where the actual part edge is on the CCD line arrays 42. Each light source 40 used in the array will emit only a certain frequency of light and each CCD line array 42 will include a filter to allow only its matched frequency to be detected. In this manner, there will be no cross-talk generated between each light source and its matched CCD line array 42.

Figure 3:
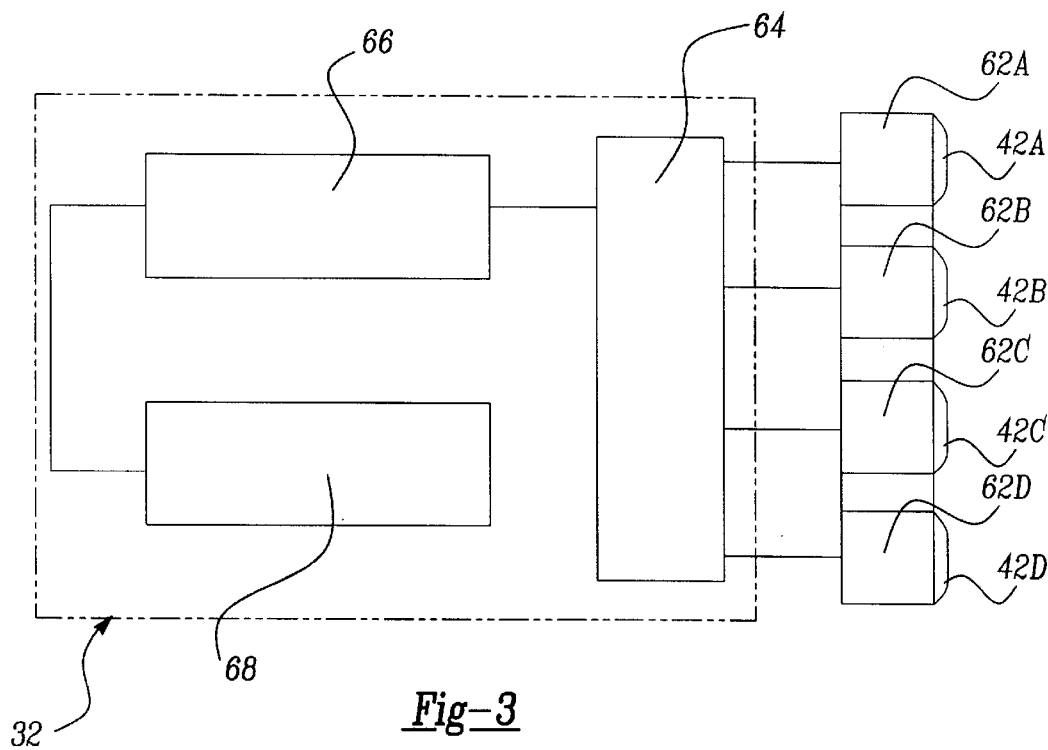
FIG. 3 is a diagram of the signal processing system of this invention.

A CCD line array is an electronic imaging device which contains a linear row of discrete photo sensing elements or pixels which convert incident light into an electrical signal. The strength of the signal is directly related to the intensity of light striking the pixels. The CCD line array generates an output signal composed of a plurality of digital and analog signals. Each pixel when saturated by an intense light can function as an "on" condition or when fully blocked can function as an "off" condition. There are also circumstances when certain pixels may be only partially blocked. During these periods, the pixels can generate analog signals proportional to the amount of light they are receiving. The CCD line array converts the incident light on each pixel into discrete charge packets. The amount of charge generated or integrated onto each pixel is a function of the integration time, and the intensity and wavelength of the light focused on the photocell. After an appropriate integration period, the charge packets are transferred simultaneously into high speed CCD shift registers 62 for transport to a signal processor 64 as shown in FIG. 3.

CCD line arrays can operate with data ranges in the megahertz or more and produce 70,000 or more scans per second. The data is also available immediately whereas a particular line from an area sensor is only available after the lines preceding it have been read out. Furthermore, the lines are sequential and are available one right after another. This makes CCD line arrays ideally suited for applications where motion is present. Typically in the present invention, a CCD line array is placed so as to align the row of pixels perpendicular to the direction of motion. That makes resolution in the direction of motion dependent on integration time, pixel size and the motion velocity. In the present invention the CCD line array can be adjusted to suit the application.

The CCD line array possesses excellent uniformity. Since a line scan camera contains a single row of pixels, the uniformity can be held much tighter than in an area array with several hundred thousand pixels. In the present invention high precision imaging applications, contrast correction hardware, and software algorithms are more easily implemented over a single line of pixels. Another valuable property of the CCD line array is that an infinitely long or continuous picture can be generated. In effect, that is what a continuously moving conveyor belt or other continuous feed system presents to the camera. The CCD line array will not chop off images as an area camera would need to in order to examine data. The CCD line array is a practical solution for the high-speed imaging of continuous feed systems.

Once the CCD line array has sampled the image it must transfer its output signals to an image processor. As seen in FIG. 3, in one embodiment of the present invention, a microcomputer such as a PC is equipped with a signal processor-I/O card 64 and interface to the CCD line arrays 42. The present invention is preferably integrated with an Intel based PC although other computers including Sun workstations, Hewlett Packard workstations, Silicon Graphics workstations, Macintosh computers, IBM workstations, Motorola microprocessor based PC's, and digital controllers may be used. The output from the CCD line arrays 42 is composed of sequential contiguous lines. These lines are processed in the order in which they are received. The shift registers 62 transfer discrete and analog information to the signal processor-I/O card 64 located in a computer 32. The signal processor 64 will interpret analog and digital information transferred by the shift registers 62, the signal processor 64 will in effect, rearrange the lines into the correct sequence. The processed data will then be stored in memory 66 to be further manipulated by microprocessor 68.

In the preferred embodiment of the present invention proprietary software has been constructed to aid in the detection of workpiece edges being examined by the inspection system. This software is designed to interpret the blurred shadows cast by the part onto the CCD line arrays 42 as it occludes the light from the diffuse light source. The pixels of the CCD line arrays 42, as discussed previously, have the ability to generate analog signals proportional to the amount of light they are receiving. The pixel signals generated by the pixels receiving the blurred shadow edges will generate signals representing a light strength gradient from those pixels completely occluded to those completely unoccluded. The software will interpret this gradient and predict where the edge of the part should be.

It is to be understood that the invention is not limited to the exact construction illustrated and described above, but that various changes and modifications may be made without departing from the spirit and scope of the invention as defined in the following claims.

What is claimed is:

1. An inspection system for evaluating workpieces for conformance to configuration criteria, comprising:
   a track means for causing said workpieces to translate through a test section, said test section including a light source for production of a uniform sheet of light, said light source oriented with respect to said track means such that said workpieces occlude said uniform sheet of light upon passing through said test section, said test section further having a video system having multi-channel intensity outputs and multiple photosensitive regions for receiving said occluded uniform sheet of light, providing an output signal related to intensity of said occluded uniform sheet of light incident on said video system, and a signal processing means for receiving said output signal.

2. The inspection system of claim 1, wherein said light source comprises:
   a coherent light source; and
   a diffractive beam shaper optically coupled to said source of light, whereby light is emitted from said coherent light source and conveyed through said diffractive beam shaper to create said uniform sheet of light.

3. The inspection system of claim 2, wherein said coherent light source is a laser.

4. The inspection system of claim 3, wherein said coherent light source is a laser diode.

5. The inspection system of claim 2, wherein said coherent light source is a diode array.

6. The inspection system of claim 1, wherein said video system comprises:
   a CCD line array;
   a lens optically coupled to said CCD line array; and
   a filter optically coupled to said lens.

7. The inspection system of claim 6, wherein said filter is configured to match a light frequency emitted by said light source, whereby stray light sources viewed by said video system may be ignored.

8. The inspection system of claim 6, wherein said CCD line array digitally samples said occluded back light.

9. The inspection system of claim 6 wherein said CCD line array includes individual pixels having individual signals proportional to the intensity of light striking said individual pixels.

10. The inspection system of claim 9, wherein said individual pixel signals are examined by a signal processor to create an image.

11. The inspection system of claim 10, wherein said signal processor examines said individual pixel signals to detect the edges of said workpiece.

12. The inspection system of claim 10, wherein said signal processor is integrated into a computer.

13. The inspection system of claim 1 further comprising a plurality of said light sources and a plurality of said video systems, each said video system matched and positioned to receive light from one of said light sources, wherein said matched video systems and light sources are oriented at angularly displaced positions surrounding said track means to sample light occluded by said workpieces at selected radial perspectives.

14. The inspection system of claim 13 wherein said plurality of light sources and said plurality of video systems may operate concurrently.

15. An inspection system for evaluating workpieces for conformance to configuration criteria, comprising:

a track means;

an adjustable slit in said track means;

a light source to provide a uniform sheet of light through said adjustable slit;

a CCD line array to receive said light through said adjustable slit and produce a plurality of digital and analog signals corresponding to said workpiece configuration.

16. The inspection system of claim 15, wherein said light source comprises:

a coherent light source; and a diffractive beam shaper optically coupled to said coherent light source, wherein light is emitted from said source of light and conveyed through said diffractive beam shaper to create a uniform sheet of light.

17. The inspection system of claim 16, wherein said diffractive beam shaper is a glass grating having an etched surface.

18. An inspection system for evaluating workpieces for conformance to configuration criteria, comprising:

a track means;

an adjustable slit in said track means;

a light source to provide a uniform sheet of light through said adjustable slit;

a one dimensional CCD line array to receive said light through said adjustable slit and produce a plurality of digital and analog signals corresponding to said workpiece configuration.

19. The inspection system of claim 18, wherein said light source comprises:

a coherent light source; and a diffractive beam shaper optically coupled to said coherent light source, wherein light is emitted from said source of light and conveyed through said diffractive beam shaper to create a uniform sheet of light.

* * * * *